United States Patent [19]
Russo

[11] Patent Number: 5,775,325
[45] Date of Patent: Jul. 7, 1998

[54] TWO PART CLOSED TRACHEAL SUCTION SYSTEM

[76] Inventor: Ronald D. Russo, 8 Candleberry Rd., Barrington, R.I. 02806

[21] Appl. No.: 691,091

[22] Filed: Aug. 1, 1996

Related U.S. Application Data

[63] Continuation of Ser. No. 438,850, May 11, 1995, Pat. No. 5,676,136.

[51] Int. Cl.⁶ ..................................................... A61M 16/00
[52] U.S. Cl. .................. 128/205.12; 128/207.14; 128/207.16; 128/912; 128/202.27
[58] Field of Search .................. 128/205.12, 207.14, 128/207.15, 207.16, 912, 202.27; 604/171, 167, 256

[56] References Cited

U.S. PATENT DOCUMENTS

| | | | |
|---|---|---|---|
| 4,960,412 | 10/1990 | Fink | 604/167 |
| 5,254,098 | 10/1993 | Ulrich et al. | 128/207.14 |
| 5,309,902 | 5/1994 | Kee et al. | 128/207.16 |
| 5,333,607 | 8/1994 | Kee et al. | 128/207.16 |
| 5,343,857 | 9/1994 | Schneider et al. | 128/207.16 |

*Primary Examiner*—Vincent Millin
*Assistant Examiner*—V. Srivastava
*Attorney, Agent, or Firm*—Robert J. Doherty

[57] ABSTRACT

A two part closed tracheal suction system comprising a first part connector for attachment to an endotracheal tube and a ventilator circuit wherein the connector includes a normally closed entrance seal directly manually accessible and preferably manually deformable to open up an access opening to the connector, and the entrance seal automatically returning to its normally closed position upon manual release of the seal.

25 Claims, 6 Drawing Sheets

TWO PART CLOSED TRACHEAL SUCTION SYSTEM

This application is a continuation of Ser. No. 08/438,850 filed May 11, 1995 now U.S. Pat. No. 5,676,136.

BACKGROUND OF THE INVENTION

This invention relates generally to closed tracheal suction devices permitting suctioning and irrigation of a patient's airway without having to disconnect the ventilator circuit to maintain PEEP (Positive End Expiratory Pressure). More particularly, the present invention is an improvement over the prior art devices disclosed in U.S. Pat. No. 3,991,762 to Radford; U.S. Pat. No. 4,569,344 to Palmer; U.S. Pat. No. 5,083,561, U.S. Pat. No. 5,220,916, and U.S. Pat. No. 5,255,676 all to Russo; and U.S. Pat. No. 5,354,267 to Niermann et. al. All these inventions along with all the other references cited give a clear picture of the prior art devices. Also U.S. Pat. No. 4,351,328 to Bodai is important in that it discloses a ventilator conduit with a resilient valve which can only be opened by inserting a suction catheter into the valve.

Furthermore, U.S. Pat. No. 5,255,676 to Russo shows a suction control valve with a structure somewhat similar to the present invention, but for an entirely different purpose for controlling fluid flow and does not teach or even contemplate the valve's use as a means for permiting the advancement and retraction of a catheter through the valve. Also, U.S. Pat. No. 274,477 to Kennish illustrates a pliable tube valve structure whose purpose is also to control fluid flow and presents no teaching of the valve's use as a non-fluid flow structure.

Many of the prior art closed tracheal suction devices are unitized in that the entire device must be disconnected from the endotracheal tube after a 24 hour period which is the effective life of the catheter assembly in terms of auto contamination. Various medical studies have shown that bacterial growth within the catheter assembly is relatively low up to a 24 hour period. However, bacterial growth then proceeds to proliferate such that all the manufacturers of closed tracheal suction devices such as Ballard Medical Inc. and Concord Labs. Inc. recommend disconnection and replacement of the entire device after 24 hours. In effect, this disconnection defeats the whole purpose of a closed system in that PEEP is eliminated and the entire replacement procedure is time consuming and will result in loss of patient ventilation during the replacement procedure. The present invention completely eliminates all of the problems and difficulties associated with this disconnection procedure while maintaining all the benefits of a closed tracheal suction system at a much lower cost.

U.S. Pat. No. 4,850,350 to Jackson describes a two part system which attempts to solve the problems and difficulties associated with unitized closed tracheal suction systems. Jackson describes a frontal coupling unit engageable with a proximal suction catheter assembly. While Jackson shows an attempt at a two part system, its main deficiency is that when the two parts are separated there is provided no automatic means for preventing loss of PEEP. A separate cap closure is needed to seal off the frontal coupling and if left unclosed could have disasterous loss of PEEP. The proximal suction catheter assembly has a rotary valve which can easily pinch the suction catheter and this rotary valve has no automatic means to close it to prevent loss of administered ventilation to atmosphere. In effect this rotary valve acts fairly similar to the stopcock type arrangement of the Niermann et. al. U.S. Pat. No. 5,354,267 device which can also crimp the catheter when the valve is rotated.

Also, U.S. Pat. No. 5,355,876 to Brodsky et. al. discloses a patient ventilating apparatus with three modular and disconnectable components comprising a patient connector, a central catheter assembly, and a rearward vacuum module. The patient connector has no seal to prevent loss of PEEP when the central catheter assembly is disconnected and the vacuum module can also become easily disconnected from the catheter assembly when the catheter is retracted resulting in dangerous loss of administered ventilation to atmosphere. The Brodsky patent is referenced only as an attempt at making a modular closed tracheal suction system, but it suffers from serious disconnection problems during use with loss of PEEP.

U.S. Pat. No. 5,513,628 to Coles et. al. is also referenced only in the fact that it discloses a ventilation circuit adapter with an internal duck bill seal that can only be opened by a separate single use catheter carrier. The catheter carrier cannot remain attached to the adapter because it permanently opens the seal to atmosphere. Therefore, vital ventilation will also be lost to atmosphere if the catheter carrier were to remain connected. A separate cap is required to close off the adapter, because Coles et. al. evidently does not have confidence that the seal will remain closed on its own when the catheter carrier is removed. The Coles et. al. patent does show an internal duck bill valve similar to Niermann et. al. U.S. Pat. No. 5,354,267 but none of these prior art valves are manually deformable by the user's hand to enable ease of insertion or retraction of a catheter on its own.

There simply is a need to have a simple, effective, low cost, two part, closed tracheal suction system which permits easy connection and disconnection of a suction catheter assembly without loss of PEEP.

In addition, reference is made to continuation pending U.S. Pat. Application No. 08/438,850 "Protective Suction Control Catheter" filed May 11, 1995, now U.S. Pat. No. 5,676,136 issued Oct. 14, 1997 to Russo, and pending U.S. Pat. Application Ser. No. 08/601,167 "Thumb Conformable Suction Control Regulator" filed Feb. 14, 1996 also to Russo which has relevant subject matter pertaining to attachment of a collapsible sheath to a suction control catheter valve and to various embodiments of a suction control regulator which can be utilized and adaptable to the present invention.

SUMMARY OF THE INVENTION

It is an object of the invention to provide the following:

1) A two part closed tracheal suction system capable of maintaining PEEP whether the two parts are connected or disconnected from each other.

2) A device comprising a ventilator connector which maintains PEEP while permitting the delivery of liquid or aerosol medication.

3) A two part closed tracheal suction system comprising a frontal closed system connector with an easily connectable and disconnectable suction catheter cartridge assembly.

4) A closed system ventilator connector capable of accepting a flexible bronchoscope or suction catheter with specimen container for both visual diagnostic procedures or for sampling secretions within a patient's airway.

5) A two part low cost closed tracheal suction system comprising a ventilator connector which can remain as part of the patient's ventilator circuit with an easily connectable suction catheter cartridge assembly which can be replaced every 24 to 48 hours as desired.

6) A suction catheter cartridge assembly providing exceptional suction efficiency with unobstructed fluid flow path and direct irrigation and flushing of the catheter permitting continued reuse of the catheter as needed.

7) A two part closed tracheal suction catheter system providing ease of insertion and retraction of the suction catheter with minimal drag or resistance to the catheter during insertion or retraction into a patient's airway.

8) A two part closed tracheal suction catheter system providing simultaneous or independent delivery of medication, bronchial lavage, or catheter flushing.

DESCRIPTION OF THE PREFERRED EMBODIMENT

Figure 1:
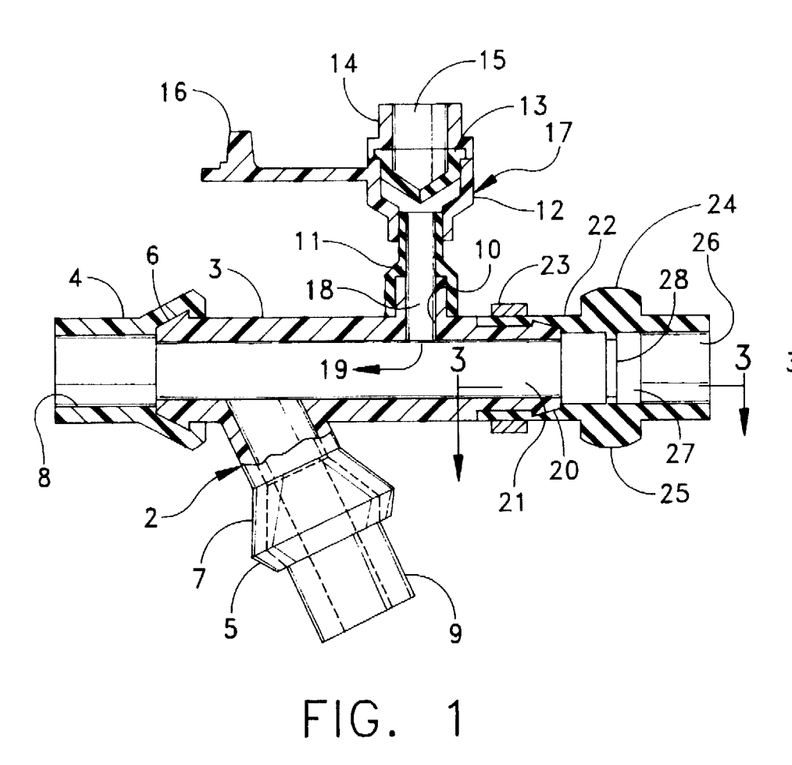
FIG. 1 is a cross sectional side view of frontal ventilator connector of the system with its manually deformable entrance seal.

Referring in detail to the drawings, there is shown in FIG. 1 a frontal swivel connector 2. The swivel connector has a body 3 into which front swivel 4 is snap fit into body 3. Side swivel 5 is also snap fit into body 3. The body and both swivels are preferably injection molded of a rigid thermoplastic typically natural translucent polypropylene. Both swivels can rotate freely 360 degrees at flared joints 6 and 7 respectively and are usually lightly lubricated with medical grade silicone lubricant to permit smooth swivel action. Internal fitment 8 on the front swivel accepts any endotracheal tube directly attached to the patient's airway. External fitment 9 on the side swivel accepts any standard ventilator breathing circuit.

Molded as part of body 3 is small bore side stem 10 which has an I.D. of 0.150 inches. Pressed onto side stem 10 is flex tubing 11 made from flexible PVC. Solvent cemented onto flex tubing 11 is lower chamber 12 injection molded of flexible PVC. Inserted into the lower chamber is silicone molded duckbill anti-reflux valve 13 which is captured by solvent cementing upper chamber 14 made from flexible PVC onto the lower chamber. Upper chamber 14 has a female luer opening 15 which will accept any standard male luer fitting. Closure cap 16 formed as part of lower chamber 12 is used to close off opening 15. This assembly forms an administration port assembly 17 capable of administering liquid or aerosol medication through stem lumen 18 into inner body passageway 19.

Rearward on body 3 is molded in barb fitting 20 with access opening 21. Press fit onto barb fitting 20 is one piece resiliently molded manually deformable entrance seal 22 which is fixedly attached to fitting 20 using stainless steel crimp band clamp 23. Once the band is crimped in place the seal becomes securely attached to body 3. The seal can be either injection molded of synthetic rubber such as Monsanto Santoprene® or molded from silicone or flourosilicone rubber of a resilient yet firm Shore A durometer of 75.

Centrally located on seal 22 is upper button 24 and lower button 25 which are formed as part of the one-piece molded seal 22. Molded internally within inner seal passage 26 is integrally molded duck bill valve 27 which has a punctured slit 28.

Figures 2, 3:
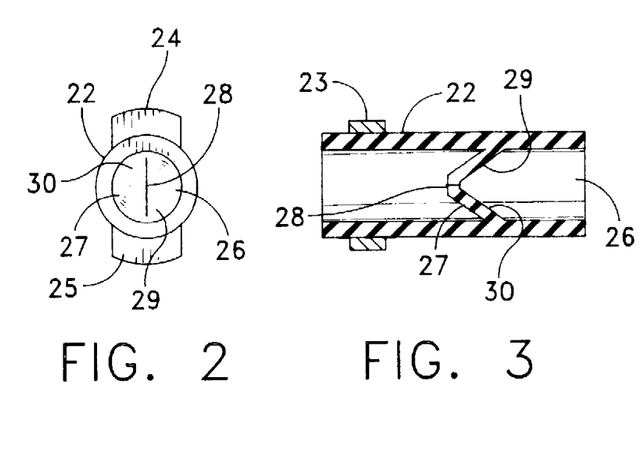
FIG. 2 is an end view of the seal in its normally closed nonactivated position.
FIG. 3 is a top cross sectional view of the seal taken along lines 3—3 in FIG. 1.

FIG. 2 is an end view of seal 22 showing slit 28 directly underneath button 24 and directly above lower button 25 and centrally in line with both buttons. On either side of slit 28 are side walls 29 and 30 of the inner duck bill valve 27.

FIG. 3 is a detailed top cross sectional view of the seal 22 which depict sidewalls 29 and 30.

Unlike the pior art duck bill valves mounted internally within the front connector (Niermann et. al. U.S. Pat. No. 5,354,267) the present invention valve 27 has thick not easily deformed side walls 29 and 30 of around 0.080 inches.

Unlike Niermann et. al. U.S. Pat. No. 5,354,267 or Bodai U.S. Pat. No. 4,351,328 neither the valve 27 nor its slit 28 can be opened by inserting a relatively soft suction catheter because the present invention uses thick side walls 29 and 30 made from firm 75 Shore A Durometer material to keep both valve 27 and side walls 29 and 30 in a normally biased closed position. As such, administration port assembly 17 with its internal anti-reflux valve 13 and entrance seal 22 with its internal duckbill valve 27 form exit seals to prevent the escape of any ventilator gases delivered through fitment 9 to atmosphere. All delivered gases will then flow into inner body passageway 19 and out internal fitment 8 into the patient's airway.

Figure 4:
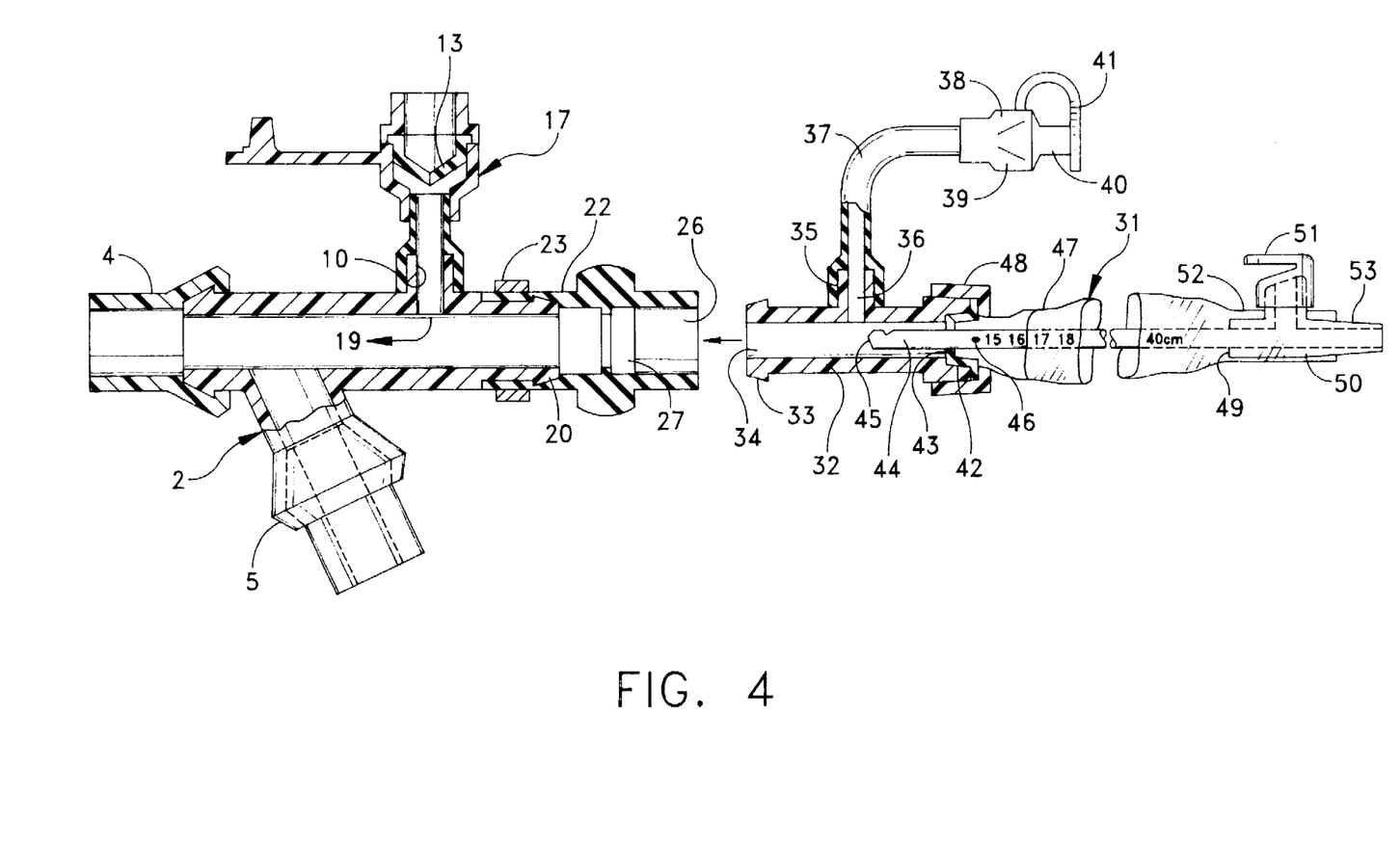
FIGS. 4 and 5 are cross sectional views of the normally separable parts of the device in separated and assembled positions respectively.

FIG. 4 illustrates frontal swivel connector 2 with all its main elements and rearward suction catheter cartridge 31. Cartridge 31 has a distal injection molded rigid barb fitting 32 with a molded in barb 33 and an inner passage 34 and the cartridge is depicted as being ready to be attached to frontal connector 2. Side stem 35 has an inner opening 36 which is a small bore about 0.150 inches in diameter. This opening 36 is in fluid communication with passsage 34 within barb fitting 32. Press fit onto stem 35 is PVC flex tubing 37 which terminates in a catheter flushing port assembly 38 virtually identical to the admnistration port assembly 17 structure illustrated as part of frontal connector 2.

Flushing port 38 has its own duck bill anti-reflux valve 39, female luer opening 40 and closure cap 41. The port 38 is solvent bonded onto flex tubing 37.

Mounted in the rear barb fitting 32 is silicone molded cup seal 42 with a thin wall opening 43 capable of forming a sliding seal around any suction catheter 44 from 8fr up to 18fr in outside diameter. The catheter open tip 45 can be any style desired such as DeLee or whistle tip. The catheter 44 can also be graduated from 15cm up to 40cm and have a black indicator mark 46. Surrounding the catheter 44 is collapsible protective catheter sheath 47 made from 1 ½ mil. thick polyethylene film.

Retaining collar 48 is injection molded of rigid thermoplastic and it securely attaches both the cup seal 42 and sheath 47 to fitting 32 by either solvent bond or snap fit.

The proximal end of the catheter 49 can be solvent bonded into suction control valve housing 50 which is capped by infection control valve cap 51. The type of housing 50 and cap 51 can be chosen from any of the types embodied in U.S. Pat. applications No. 08/438,850 or No. 08/601,167 both to Russo now pending.

The attachment of the rear portion 52 of sheath 47 to housing 50 is also described as the preferred method of attachment in pending U.S. Pat. application No. 08/438,850 to Russo. Tapered suction connector 53 on housing 50 permits direct connection to a suction source.

Figure 5:
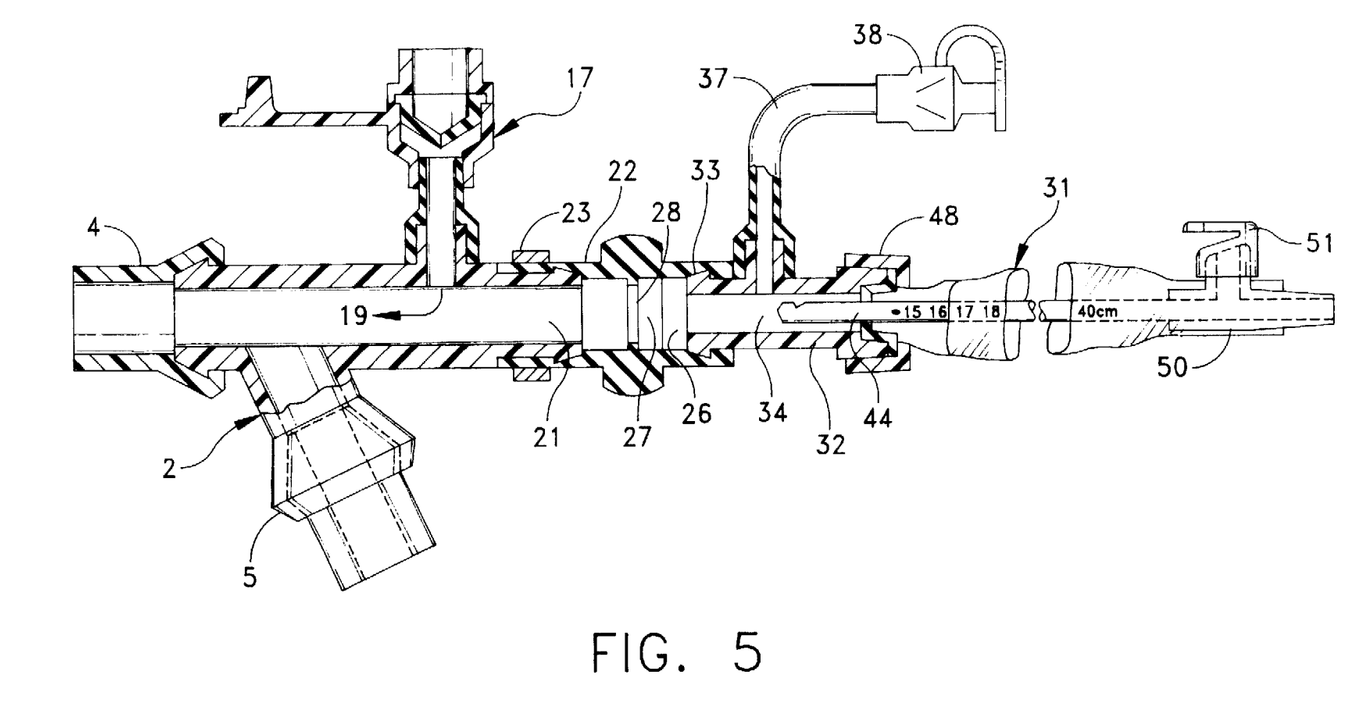

FIG. 5 illustrates frontal swivel connector 2 attached to rearward catheter cartridge 31. As can be seen rigid barb fitting 32 can be press fit inserted into inner seal passage 26 to form a sealing engagement between connector 2 and cartridge 31.

Figure 6:
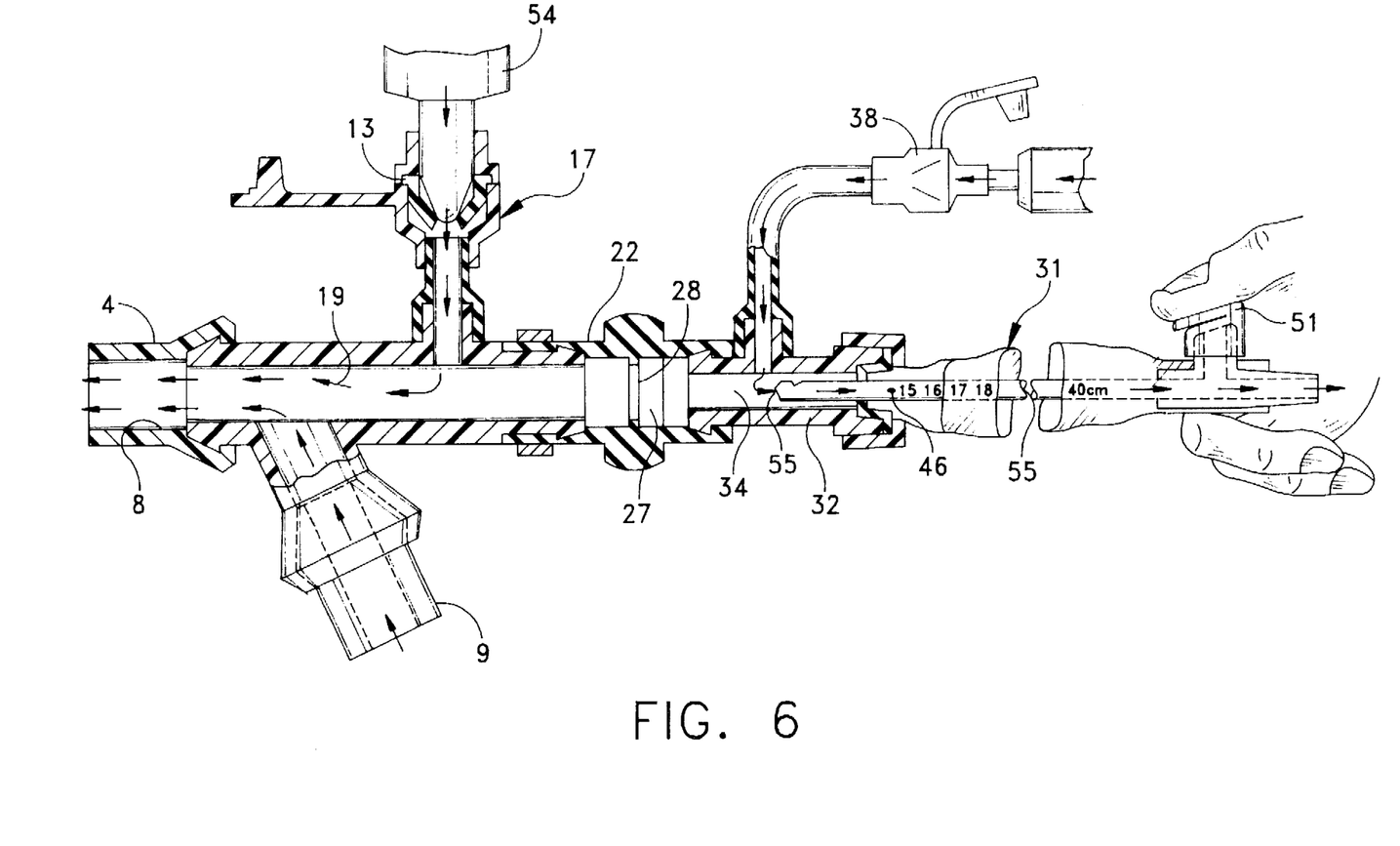
FIG. 6 is a cross sectional side view of both parts of the device connected together depicting frontal delivery of medication into the connector with simultaneous delivery of irrigation flushing solution into the catheter cartridge assembly.

FIG. 6 clearly illustrates how the administration port assembly 17 can be used to deliver medication or bronchial lavage into inner body passageway 19 and into a patient's airway. Fluid delivery can be delivered through opening duck bill valve 13 using unit dose vials, aerosol canisters, or by luer syringe methods. Every time ventilator gases are delivered through side swivel 9 they become co-mingled with the medication administered through port 17 to be driven down deep into a patient's airway to loosen secretions for improved breathing and for more effective suctioning away of accumulated mucous by the suction catheter.

The entrance seal 22 with its normally closed valve 27 acts as a positive seal to make sure that all administered medication through port 17 goes into a patient's airway and none can escape through the seal. Likewise, when flushing or cleaning of the catheter is needed flushing can take place through flushing port assembly 38. The entrance seal 22 only permits flushing fluid to enter passage 34 of fitting 32. Activation of cap 51 applies suction to permit flushing fluid to be aspirated into the suction lumen 55 to both clean the lumen 55 and also the entire suction system line. The administration of medication through port 17 and the flushing of the catheter through port 38 can take place separately or simultaneously as illustrated in FIG. 6.

Figure 7:
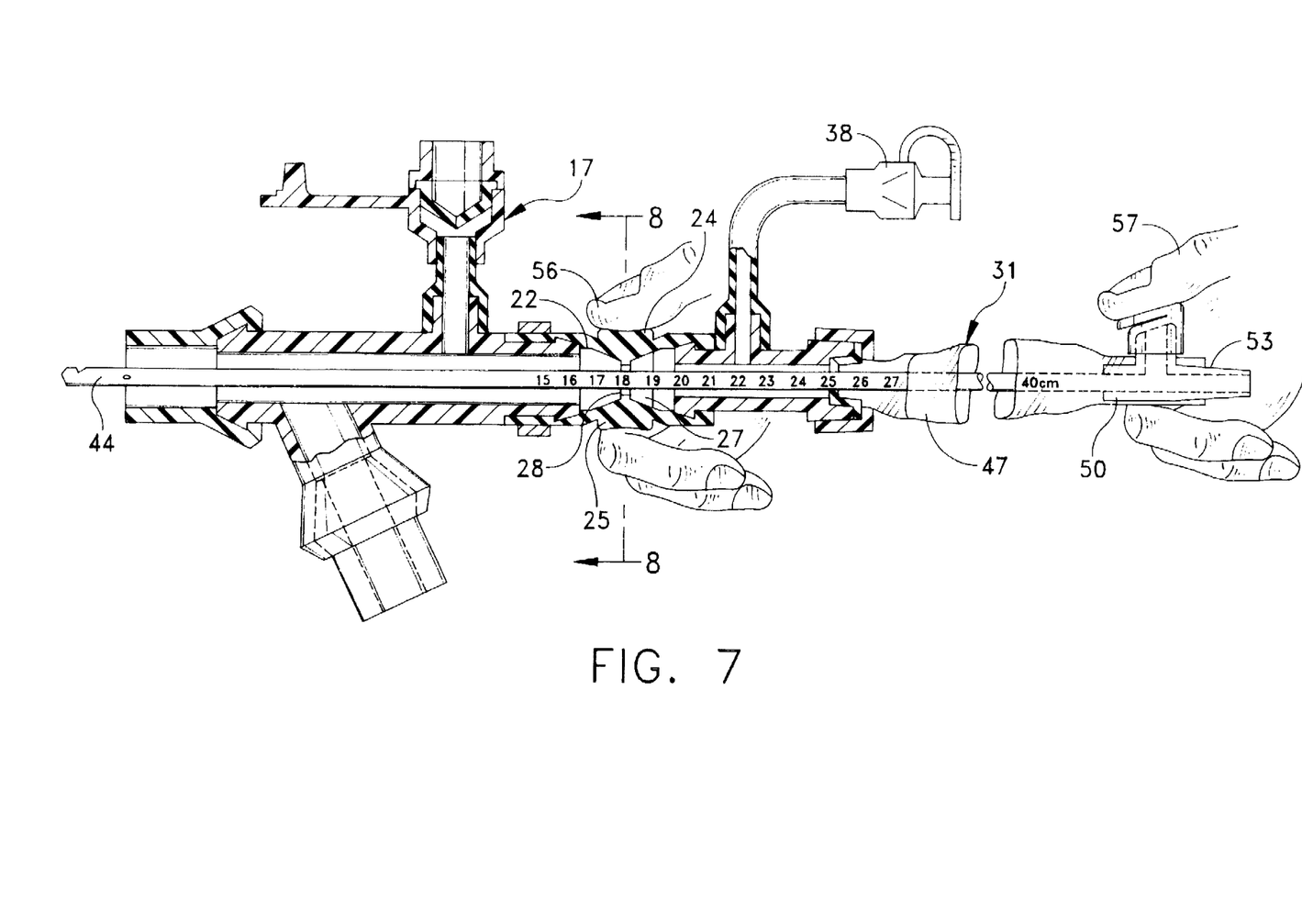
FIG. 7 is a cross sectional side view depicting manual opening of the entrance seal with advancement of the catheter through the entrance seal and into a patient's airway.

In summary, entrance seal 22 effectively acts as a sealing barrier between connector 2 and cartridge 31. Advancement of the catheter will not open seal 22 or duck bill valve 27 or slit 28. As illustrated in FIG. 7 only manual depression of both buttons 24 and 25 with one hand 56 will open up slit 28 on valve 27 to permit simultaneous advancement of the catheter by other hand 57. This procedure will permit advancement of the catheter as far as desired and so long as the seal 22 is depressed the catheter can easily slide in and out of the patient's airway. Once the buttons are released the catheter is actually retained by seal 22. This is a novel arrangement in that the catheter is automatically retained in place by valve sidewalls 29 and 30 acting on the catheter 44 such that medication can be delivered through port 17 which will drip down the catheter deep into a patient's airway for bronchial lavage. Retraction of the catheter while still depressing on seal 22 will bring it back behind slit 28 to permit flushing of the catheter as illustrated in FIG. 6.

Figure 8:
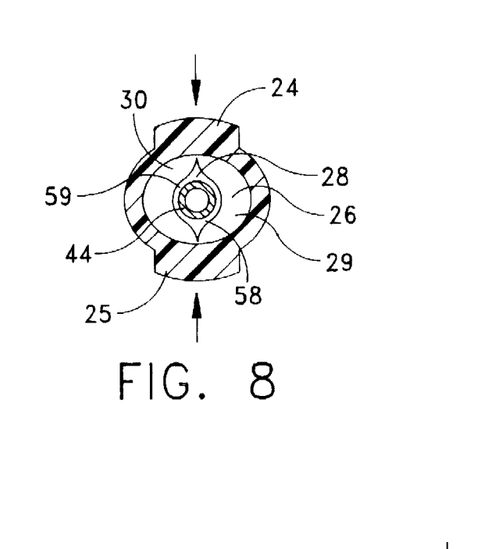
FIG. 8 is a cross sectional view of the manually activated entrance seal with the catheter inserted into the entrance opening of the seal taken along lines 8—8 in FIG. 7.

FIG. 8 clearly shows how catheter 44 can be easily inserted into slit 28 when buttons 24 and 25 are depressed which causes side walls 29 and 30 to flex sidewards to purse open slit 28. Further, inner seal passage 26 is large enough (about ½ inch internal diameter) to permit slit 28 to open just wide enough to permit easy insertion of any size suction catheter, while still maintaining PEEP without creating any drag or resistance on the catheter as shown by slight gaps 58 and 59 surrounding the catheter.

Figure 9:
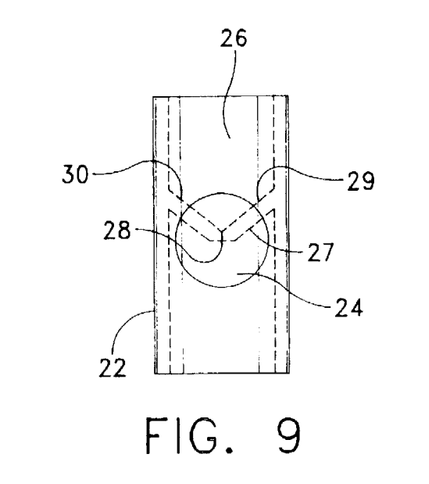
FIG. 9 is a top view of the entrance seal showing the internal duck bill valve.

FIG. 9 depicting a top view of the entrance seal 22 in its normally closed position clearly shows slit 28 sealed closed.

Figure 10:
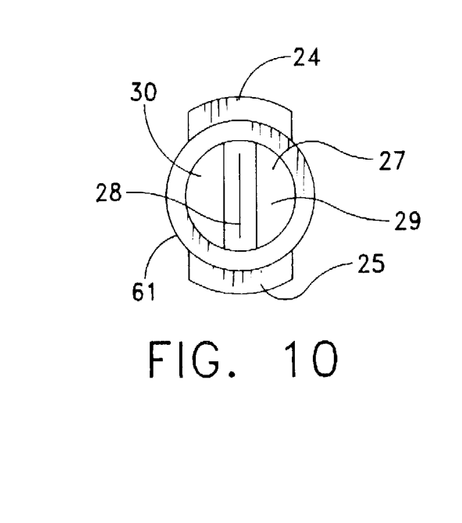
FIG. 10 is a front view of the entrance seal of FIG. 9 clearly showing the internal duck bill valve in its normally closed position.

FIG. 10 which is a front view of the seal also depicts slit 28 sealed closed when the duckbill valve 27 is not manually depressed.

Figure 11:
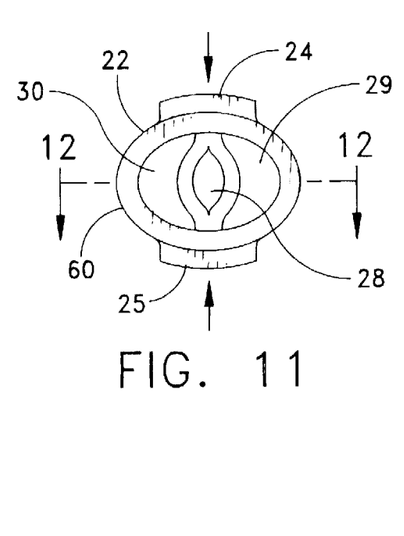
FIG. 11 is a front view of the entrance seal in its manually deformed state showing the slit opening pursed open.

In FIG. 11 which is also a front view of the seal, buttons 24 and 25 are shown depressed which purses open slit 28 using flexible side walls 29 and 30. The outer wall 60 of seal 22 will also slightly deform into an oval shape in the area of the seal 22 depressed by buttons 24 and 25, once the valve 27 is no longer manually deformed it will return to its normally closed state shown in FIG. 10 and outer wall 60 shown in FIG. 11 will return to its normal round or circular state 61 as shown in FIG. 10.

Figure 12:
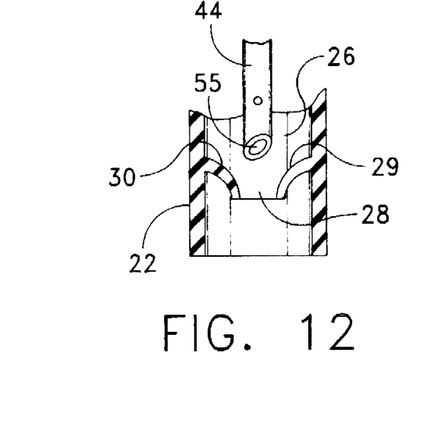
FIG. 12 is a partial top cross sectional view of the entrance seal taken along lines 12—12 of FIG. 11 showing the slit opening pursed open.

FIG. 12 is a partial top cross sectional view of the seal showing slit 28 pursed open by flexing sidewalls 29 and 30 caused by manual deformation of the valve. Catheter 44 with its lumen 55 is shown ready for forward advancement into slit 28.

Once the catheter is fully retracted back into its cartridge when the suctioning procedure is completed and the indicator mark 46 is clearly visible then in essence the catheter cartridge becomes completely isolated from its neighboring swivel connector 2. However, the suction catheter cartridge 31 is always ready for use and repeated suctioning can take place as often as needed. After a 24 or 48 hour time period, whichever is the hospital's choice or protocol, the catheter cartridge can be removed from the frontal connector 2 by gently pulling back on fitting 32 of the cartridge while holding connector 2 and the cartridge can be separated and replaced with a new sterile catheter cartridge while the connector remains as part of the ventilator circuit. This means that there is no loss of PEEP during removal or replacement of the cartridge. Also the system becomes much less expensive since the connector part remains with the patient and only the cartridge needs replacing. Another desirable feature of this two part system is the ability to permit bronchoscopic examination of the patient's airway or sputum samples to be taken directly through the entrance seal. To accomplish this the cartridge must be disconnected to permit intubation of the bronchoscope or sputum sampler directly into the entrance seal by manual depression of the entrance seal while advancing the scope or sampler. Afterwards, the cartridge can be reattached to the swivel connector 2. This also maintains PEEP and means that the ventilator need not be disconnected during suctioning, bronchoscopic examination, or sputum sampling. Presently, commercially available closed tracheal suction systems are unitized and the entire device must be disconnected from the ventilator every 24 or 48 hours which means loss of PEEP and trauma to the patient resulting from disconnection.

It will be understood that many variations and modifications may be made in the present invention without departing from the spirit and scope thereof. While there is shown the most preferred embodiment therein, variations such as a non-swiveled connector, or a connector with only one swivel, or the use of only one flushing or administration port, or the removal of anti-reflux valves in the ports can be made without departing from the basic invention. Also, the catheter cartridge can vary in its means for attachment to the entrance seal, as well as different style sheaths, sheath retaining means, or suction control valves, whether normally open to atmosphere or normally closed to atmosphere, without departing from the scope and breadth of the invention.

The duck bill valve shown could take other forms, e.g., the diaphragm shown and described in Russo's U.S. Pat. No. 5,255,676, so long as the application of external force on that portion of the connector defining the valve serves to open the valve seal rather than by the insertion of a device such as a suction catheter or bronchoscope although the situation wherein the seal is opened in both manners is not ruled out. Also although the present invention specifically describes opening the front connector seal via application of opposed manual force application by one hand of the operator, other manners which utilize force application on external portions of the connector which serve to open the seal are contemplated as well whether they include manual or mechanical force application or some combination of such. Also, it should be pointed out that the present device, although described as a two-part device, does not rule out its formation in more than two separable pieces—the essential feature being that the frontal connector attached to the patient forms one part of a system which is detachable therefrom without loss of PEEP. In other words, further separation of those portions of the device upstream of the frontal connector is optional. Also, the control valve 50 of the present invention could take other forms including but not limited to those shown in my previously referred to patents, namely, U.S. Pat. Nos. 5,220,916 and 5,255,676 as well as in my previously referred to pending applications, Ser. Nos. 08/438,350 and 08/601,167, and the disclosures of which are herein incorporated into the present specification by specific reference thereto.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A connector for use in a ventilator system including a conduit adapted for connection between a patient's trachea via an endotracheal tube and a respirator, said connector having a body defining a first opening for connection to the endotracheal tube and a second opening for connection to the respirator; the improvement comprising said body defining a third opening generally oriented opposite said first opening and wherein said third opening is normally biased closed by an entrance seal valve positioned in said body, said valve including a structural portion located on the outside of said body and operable by depressing directly manually from the outside of said body during operation of the ventilator system so as to move and maintain said valve to and in an open position by the continual and direct application of external force to said valve structural portion, said valve automatically adapted to return to its normally closed position when said force application is removed, said valve permitting entrance and removal of a suction tube into and through said third opening when said valve is opened.

2. The connector of claim 1, said valve structural portion being deformable by the manual application of force thereto.

3. The connector of claim 2, said connector body having opposed sides and said manual force application structural portions externally positioned on said opposite sides of said body whereby said manual force application is created by one handed force application to said force application structural portions.

4. The assembly of claim 2 wherein the manually deformable valve is of duck bill configuration with a pre-slit opening therethrough for opening and closing said valve.

5. The assembly of claim 2 wherein the valve includes walls having an internal pre-slit opening which is normally biased closed, said walls deformable to open said opening by said continual and direct manual application of force to said structural portion.

6. The assembly of claim 1 wherein the connector is part of a normally closed to atmosphere tracheal suction system.

7. The assembly of claim 1 wherein the connector has at least one swivel opening.

8. The assembly of claim 1 wherein the connector includes an administration port for delivery of fluid.

9. The assembly of claim 1 wherein the suction tube is a flexible suction catheter.

10. The method of endotracheal suctioning of a breathing patient who is connected to an endotracheal tube and a gaseous respirator circuit including a connector conduit that maintains positive end expiratory pressure within the lungs of the patient, comprising the steps of:

providing an opening in said conduit near the endotracheal tube which is normally substantially closed off by an entrance seal with an opening biased to normally maintain the opening closed;

opening the seal by the application of external force to a structural portion located on the outside of the conduit so as to permit the entrance of a suction tube therethrough; thereafter passing the suction tube through said opening and thence into a patient's lungs through the endotracheal tube by continuing to advance the suction tube into the patient's lungs while maintaining the seal to its open position by the continual application of said external force; and thereafter suctioning the lungs of the patient to remove fluid therefrom through the suctioning tube, and removing the suctioning tube from said conduit through said seal once suctioning is completed, whereby the opening closes once the suctioning tube is removed, and the valve is no longer maintained in its open position so as to maintain positive end expiratory pressure within the circuit.

11. The method of claim 10 wherein said seal is opened by the manual application of force.

12. A closed tracheal suction system having at least two separable parts, comprising a first part frontal connector having a body including a first opening connected to a patient's endotracheal tube, a second opening connected to a respirator for delivery of ventilation into the endotracheal tube, and a third opening including a normally biased closed entrance seal which includes a means for attachment of a second part suction catheter assembly, said seal having structural portions located on the outside of said body on directly manually operable from the outside of said body to move and maintain said seal to and in an open position by the application of external force to said structural portions to permit advancement of the suction catheter into the first opening and on into the patient's endotracheal tube for suctioning, said seal returning to its normally biased closed position upon retraction of the suction catheter and release of the external force on said entrance seal.

13. The assembly of claim 12 wherein the connector has at least one swivel.

14. The assembly of claim 12 wherein the connector remains connected to the respirator while the catheter assembly can be removed and replaced.

15. The assembly of claim 12 wherein the connector maintains positive end expiratory pressure.

16. The assembly of claim 12 wherein the connector includes a port for delivery of fluid for bronchial lavage.

17. The assembly of claim 12 wherein the catheter assembly includes means for flushing the catheter without having to disconnect the assembly from the connector.

18. In combination with a medical device which is capable of applying suction to a patient by the operation of said device which in turn includes a connector assembly for attachment to the patient and having a first opening adapted for receipt of a patient's endotracheal tube, a second opening adapted for receipt of a respirator for delivery of positive pressure ventilation into the endotracheal tube and a third opening adapted for receipt of a suction catheter assembly in turn including a catheter adapted for advancement into and through said connector assembly and into said endotracheal tube, said connector including a one-piece molded body-including an internal conduit defining a passageway between said first and third openings and said connector body having wall portions located on the outside of said body and directly manually operable by the direct manual application of force thereto and a deformable integral valve portion extending across said passageway and normally closing said passageway deformable to an open valve position by the direct manual application of force to said wall portions and wherein said conduit includes means for detachably receiving said suction catheter assembly.

19. The connector assembly of claim 18, said conduit including front and rear ends and wherein said conduit front end operatively positioned at said third opening and wherein said conduit rear end includes said means for detachably receiving said catheter assembly.

20. The assembly of claim 18, said connector including a fluid installation port permitting installation of fluid into said passageway.

21. The method of claim 10 wherein said seal is deformable to its open position.

22. The method of claim 21, wherein said seal includes deformable walls having an internal preslit opening therein, said walls deformable to open said opening by direct application of manual force to said body conduit.

23. The closed tracheal suction system of claim 12 wherein said seal is deformable to its open position.

24. The closed tracheal suction system of claim 23, wherein said seal includes deformable walls having an internal pre-slit opening therein, said walls deformable to open said opening by direct application of manual force to said body conduit.

25. The connector of claim 1, said valve preventing the entrance therethrough of an implement when said valve is in the closed position.

* * * * *